United States Patent [19]

Klein et al.

[11] 3,997,615
[45] Dec. 14, 1976

[54] PROCESS FOR RECOVERY OF ORTHO-PHENYLPHENOL

[75] Inventors: Joseph F. M. Klein, Bunde; Petrus A. M. J. Stijfs, Munstergeleen; Josef A. Thomas, Sittard, all of Netherlands

[73] Assignee: Stamicarbon B.V., Geleen, Netherlands

[22] Filed: May 20, 1975

[21] Appl. No.: 579,053

[30] Foreign Application Priority Data

May 24, 1974 Netherlands ................... 7406965

[52] U.S. Cl. .......................... 260/620; 260/619 D
[51] Int. Cl.$^2$ ................. C07C 37/34; C07C 37/28
[58] Field of Search ...................... 260/620, 619 D

[56] References Cited

FOREIGN PATENTS OR APPLICATIONS 1,327,581   8/1973   United Kingdom ............... 260/620

*Primary Examiner*—Norman Morgenstern
*Attorney, Agent, or Firm*—Cushman, Darby & Cushman

[57] ABSTRACT

A process for purifying ortho-phenylphenol which is admixed with ortho-cyclohexylphenol, by treating the mixture with an alkaline solution containing less than one mole equivalent of base per mole of ortho-phenylphenol in said mixture; the alkaline solution is extracted and ortho-phenylphenol is recovered from the aqueous phase by acificiation and extraction with subsequent isolation of the ortho-phenylphenol, which contains less than 5% (by weight) ortho-cyclohexylphenol.

6 Claims, No Drawings

PROCESS FOR RECOVERY OF ORTHO-PHENYLPHENOL

BACKGROUND OF THE INVENTION

The invention relates to a process for the recovery of the well-known preservative ortho-phenylphenol from a mixture containing such compounds as ortho-cyclohexylphenol, ortho-cyclohexylcyclohexanone, biphenyl and diphenylene oxide in addition to the ortho-phenylphenol.

Ortho-phenylphenol can be prepared by the dehydrogenation of 2-cyclohexenyl cyclohexanone, as disclosed in British patent specification No. 1,327,581; when ortho-phenylphenol is produced by said dehydrogenation method it is admixed with ortho-cyclohexylphenol, cyclohexylcyclohexanone, biphenyl and diphenylene oxide.

For use in commercial processes, the ortho-phenylphenol to be separated from such a mixture must have an ortho-cyclohexylphenol content not exceeding 5% by weight in order to be used as a carrier for dyestuffs in the textile industry and for any other application. The British Patent Specification mentioned above, discloses recovering ortho-phenylphenol from the crude reaction mixture obtained in the dehydrogenation by treating the reaction mixture with excess hydroxide solution (said excess based on the total amount of phenols present); filtering off the diphenylene oxide which then precipitates subjecting the filtrate to steam distillation; acidifying the remaining residue and extracting with ether, and then distilling the resulting product. The resulting distillate, which still contains the original amount of ortho-cyclohexylphenol in addition to the ortho-phenylphenol, can then be dehydrogenated catalytically to convert ortho-cyclohexylphenol into ortho-phenylphenol but with concomitant formation of other additional impurities.

It has now been found that this expensive processing method can be simplified considerably and a product can be obtained which contains no impurities apart from a small amount of ortho-cyclohexylphenol.

SUMMARY OF THE INVENTION

The process according to the invention is directed to a method of purifying and recovering ortho-phenylphenol with an ortho-cyclohexylphenol content of less than 5% by weight from a reaction mixture containing more than 0.05 gram of ortho-cyclohexylphenol per gram of ortho-phenylphenol. In accordance with the invention, a reaction mixture, containing ortho-cyclohexylphenol and ortho-phenylphenol, is treated with an aqueous hydroxide solution wherein less than 1 mole-equivalent of hydroxide (in solution) is used per mole of ortho-phenylphenol; the resulting alkaline mixture is subjected to an extraction with an organic solvent; and the ortho-phenylphenol is recovered from the aqueous phase obtained in the extraction.

In the process according to the invention, ortho-phenylphenol containing only a small amount of ortho-cyclohexylphenol can be obtained from the aqueous phase, e.g. by acidification of the aqueous phase followed by extraction; and, this process obviates the necessity of the step of separate catalytic after-treatment to convert cyclohexylphenol to ortho-phenylphenol. Filtration is not a necessary step in this invention. Fractional distillation of the organic phase obtained in the extraction of the alkaline mixture with the organic solvent will contain, in addition to the organic solvent ortho-cyclohexylphenol and ortho-phenylphenol which has not dissolved in the aqueous phase.

DETAILED DESCRIPTION OF THE INVENTION

The invention is directed to recovering ortho-phenylphenol from a mixture containing also ortho-cyclohexylphenol. By treating a mixture containing ortho-phenylphenol and ortho-cyclohexylphenol with an amount of base which is less than a mole equivalent of the ortho-phenylphenol in said mixture to form an alkaline mixture; extracting the alkaline mixture with an organic solvent, and recovering the ortho-phenylphenol from aqueous layer, ortho-phenylphenol may be isolated containing less than 5% by weight of ortho-cyclohexylphenol.

This process is particularly suitable in purifying and isolating ortho-phenylphenol which is produced by dehydrogenation of 2-cyclohexyl cyclohexanone. The dehydrogenation of 2-cyclohexyl cyclohexanone and the resulting products are disclosed in British patent specification No. 1,327,581 which is incorporated herein by reference. When ortho-phenylphenol is produced by dehydrogenation of 2-cyclohexyl cyclohexanone, it is admixed with ortho-cyclohexylphenol, cyclohexylcyclohexanone; biphenyl and diphenylene oxide. By using the improvement of the invention, i.e. treating the reaction mixture with less than one mole equivalent of base per mole of said ortho-phenylphenol, the laborious, costly and inefficient method of recovering ortho-phenylphenol, as disclosed in British patent specification No. 1,327,581 is simplified and rendered more efficient. The process of separating ortho-phenylphenol, from the reaction mixture, according to this reference requires treating the reaction mixture with excess aqueous hydroxide (based on total amount of phenols produced); filtering (diphenylene oxide) from the alkaline mixture; steam distilling the filtrate; acidifying the residue; extracting with ether; distilling the product; and catalytically dehydrogenating the distilled mixture to convert, all ortho-cyclohexylphenol produced in the original reaction and admixed with ortho-phenylphenol, to ortho-phenylphenol.

By comparison, the process in accordance with the invention comprises admixing the reaction mixture (produced by the dehydrogenation of 2-cyclohexylcyclohexanone) with an amount of base (aqueous solution) which is less than a mole equivalent of the ortho-phenylphenol contained in the reaction mixture. To isolate ortho-phenylphenol containing less than 5% by weight ortho-cyclohexylphenol, the alkaline aqueous reaction mixture is extracted with an organic solvent and the ortho-phenylphenol is isolated from the aqueous layer. In accordance with one embodiment of the invention, the ortho-phenylphenol is isolated by acidification of the alkaline layer, followed by extraction with an organic solvent.

The amount of base used in the alkaline solution is less than a molar equivalent of hydroxide per mole of ortho-phenylphenol in the mixture. The amount of ortho-phenylphenol in the mixture is determined by gas-chromatographic analysis.

In calculating the amount of ortho-phenylphenol, the amount of said compound in the phenolate form is included. The determination of the amount of hydroxide solution required for the formation of phenolate includes the amount required for the formation of phenolate.

In the process according to the invention, the aqueous hydroxide solutions used may be aqueous solutions of various hydroxides and salts showing an alkaline reaction. In particular metal hydroxides and metal carbonates can be used. Examples of suitable hydroxides are sodium hydroxide, potassium hydroxide, barium hydroxide, magnesium hydroxide, and calcium hydroxide. Examples of salts showing an alkaline reaction are sodium carbonate and potassium carbonate. The concentration of these solutions of hydroxides and/or salts may be varied, e.g. between 5 and 150 grams, preferably between 10 and 50 grams of hydroxide and/or salt per liter of solution. As long as the base is used in amounts less than a mole equivalent of ortho-phenylphenol, the exact amount of base can be varied. A highly satisfactory result can be obtained if 0.3 – 0.8 mole-equivalent of hydroxide solution is used per mole of ortho-phenylphenol. Furthermore, the process according to the invention may be carried out at ambient temperature. The most suitable temperature is naturally determined in part by the boiling point of the extraction agent. Use may, for instance, be made of a temperature between 10° and 90° C.

For the extraction of the alkaline mixture and, if so desired, for the recovery of the ortho-phenylphenol by extraction from the acidified aqueous phase, use may be made of various inert organic solvents, such as, e.g., toluene; benzene; o-, m-, and p-xylenes and cyclohexane. The extraction agent required for the extraction of the alkaline mixture may be added entirely or partly before the treatment with the aqueous hydroxide solution. If no extraction agent is present in the treatment with hydroxide solution, this treatment is effected at elevated temperature, e.g. 80° C. to prevent crystallization.

In the step of acidification of the alkaline solution of the mixture containing ortho-phenylphenol, ortho-cyclohexylphenol, cyclohexylcyclohexanone, biphenyl and diphenylene oxide, sulfuric acid is conveniently employed, although other acids, such as nitric acid and hydrochloric acid, may also be employed.

The process according to the invention may be carried out by dissolving the reaction mixture, which may have been obtained, e.g., from the dehydrogenation of 2-cyclohexenyl cyclohexanone in the liquid or gaseous phase, in an organic solvent, bringing the resulting solution into contact with one or several series-connected stages of the base treatment in accordance with the invention with simultaneous stirring, separating the resulting mixture into two layers, and recovering the ortho-phenylphenol from the aqueous layer after this has been acidified.

Another suitable realization is bringing a solution of the reaction mixture into contact with the hydroxide solution in counter-current relation. This can, for instance, be effected in a so-called rotating-disc contactor or in a pulsation column, wherein optionally, portions of the hydroxide solution may be fed to the column at various heights. If the process is effected in several stages, wherein part of the required amount of hydroxide solution is added in each stage, naturally the amount of hydroxide solution used is present in the required amount, i.e., less than 1 mole equivalent with respect to the amount of ortho-phenylphenol, at least in the stage from which the aqueous phase to be processed further is discharged.

The process according to the invention will be further eluciated in the following examples.

EXAMPLE I 60 grams of a mixture composed of 83.3% by weight of ortho-phenylphenol (hereinafter abbreviated as OPP) and 16.7% by weight of orthocyclohexylphenol (hereinafter abbreviated as CHP) were dissolved in 40 ml of toluene. This solution was shaken in a separatory funnel at room temperature with 352.8 grams of aqueous sodium-hydroxide solution (2.5% by weight), which corresponds to 0.75 mole-equivalent of hydroxide solution per mole of OPP. After two layers had formed, the aqueous layer was drained off and acidified to a pH of 4.5 with 11.2 grams of sulphuric acid (96% by weight). The resulting product was extracted with toluene several times. After evaporation of the toluene, 35.7 grams of OPP were obtained, which contained only 3.5% by weight of CHP, determined by gas-chromatographic analysis.

EXAMPLE II

Example I was repeated with the difference that the solution was shaken with 117.5 grams of aqueous sodium-hydroxide solution (5.0% by weight), which corresponds to 0.50 mole-equivalent of hydroxide solution per mole of OPP. The yield was 25.2 grams of OPP which contained 3.7% by weight of CHP according to gas-chromatographic analysis.

EXAMPLE III 60 grams of a mixture composed of 83.3% by weight of OPP and 16.7% by weight of CHP were dissolved in 40 ml of toluene and shaken at room temperature with 352.8 grams of aqueous sodium-hydroxide solution (2.5% by weight), which corresponds to 0.75 mole-equivalent of hydroxide solution per mole of OPP. After the two layers had separated, the hydroxide solution was extracted twice with toluene, and, next, acidified with 11 grams of sulphuric acid (96% by weight). After the liberated phenols had been extracted with toluene and the toluene had been evaporated, 30 grams of OPP were obtained, which contained 0.9% by weight of CHP according to gas-chromatographic analysis.

EXAMPLE IV 45.2 grams of a reaction mixture obtained by dehydrogenation of 2-cyclohexenyl cyclohexanone and composed of 60% by weight of OPP, 12% by weight of CHP, 19% by weight of biphenyl, 6.5% by weight of cyclohexyl cyclohexanone, and 2.5% by weight of diphenylene oxide were dissolved in 20 ml of toluene. This solution was shaken at room temperature with 95.6 grams of aqueous sodium-hydroxide solution (5% by weight), which corresponds to 0.75 mole-equivalent of hydroxide solution per mole of OPP. After the organic layer and the aqueous layer had separated, the latter was extracted twice with toluene and then acidified to a pH of 4.5 with 6 grams of concentrated sulphuric acid. The product thus obtained was extracted with toluene, and, after evaporation of the toluene, 20 grams of OPP were left, which contained 2.0% by weight of CHP and less than 0.02% by weight of diphenylene oxide according to gas-chromatographic analysis. No other impurities were present. The organic layer obtained in contact with the sodium-hydroxide solution was subjected to fractional distillation, when biphenyl and diphenylene oxide and a fraction containing OPP, CHP, and 2-cyclohexenyl cyclohexanone were separated off.

EXAMPLE V

Example I was repeated with the difference that 40 ml of cyclohexane were used instead of 40 ml of toluene. The CHP content of the resulting product amounted to 4.2% by weight.

What is claimed is:

1. In a process for separating ortho-phenylphenol, from a mixture containing ortho-cyclohexylphenol cyclohexylcyclohexanone, biphenyl and diphenylene oxide, comprising treating the mixture with excess aqueous hydroxide, based on the total amount of phenols present in the mixture to isolate the ortho-cyclohexylphenol and ortho-phenylphenol as a second mixture; and catalytically dehydrogenating said second mixture to convert, ortho-cyclohexylphenol to ortho-phenylphenol, the improvement comprising treating said mixture with an amount of base which is less than a mole equivalent of the ortho-phenylphenol contained in the mixture, to form an alkaline medium containing said mixture; extracting the alkaline solution of said mixture with an inert organic solvent which is toluene, benzene, o-xylene, m-xylene, p-xylene or cyclohexane; acidifying said alkaline medium, and separating said ortho-phenylphenol from said acidified medium, thereby obviating said step of catalytic dehydrogenation to convert ortho-cyclohexylphenol to ortho-phenylphenol.

2. The process of claim 1, wherein said step of separating comprises extracting said acidified medium with an inert organic solvent.

3. The process of claim 1, wherein said alkaline solution contains 0.3 to 0.8 mole-equivalent of hydroxide solution per mole of ortho-phenylphenol.

4. The process of claim 1, characterized in that use is made of an aqueous hydroxide solution with a concentration of between 10 and 50 grams of hydroxide and/or salt per liter of solution.

5. In a process for separating ortho-cyclohexylphenol from ortho-phenylphenol, which are admixed with cyclohexylcyclohexanone, biphenyl and diphenylene oxide, by treating the mixture with a base to separate ortho-phenylphenol from a mixture which contains in addition, ortho-cyclohexylphenol, cyclohexyl cyclohexanone, biphenyl and diphenylene oxide and extracting said basic mixture with an organic solvent; recovering ortho-phenylphenol from the basic mixture, the improvement comprising treating said mixture with a base in an amount which is less than a molar equivalent of said ortho-phenylphenol.

6. The process of claim 5, wherein said base is a metal hydroxide which is employed in an amount of 0.3 to 0.8 moles per mole of said ortho-phenylphenol.

* * * * *